United States Patent
Taylor et al.

(10) Patent No.: US 8,112,152 B2
(45) Date of Patent: *Feb. 7, 2012

(54) FEEDTHROUGH APPARATUS WITH NOBLE METAL-COATED LEADS

(75) Inventors: William J. Taylor, Anoka, MN (US); Lynn M. Seifried, Minneapolis, MN (US); William D. Wolf, St. Louis Park, MN (US); Andrew J. Ries, Lino Lakes, MN (US); John E. Kast, Hugo, MN (US)

(73) Assignee: Medtronic, Inc., Minneapolis, MN (US)

( * ) Notice: Subject to any disclaimer, the term of this patent is extended or adjusted under 35 U.S.C. 154(b) by 255 days.

This patent is subject to a terminal disclaimer.

(21) Appl. No.: 12/397,774

(22) Filed: Mar. 4, 2009

(65) Prior Publication Data

US 2009/0163974 A1   Jun. 25, 2009

Related U.S. Application Data

(63) Continuation of application No. 10/661,919, filed on Sep. 12, 2003, now Pat. No. 7,966,070.

(51) Int. Cl.
*A61N 1/375* (2006.01)

(52) U.S. Cl. .......................... 607/36; 607/37
(58) Field of Classification Search ............... 607/36–37
See application file for complete search history.

(56) References Cited

U.S. PATENT DOCUMENTS

| | | | |
|---|---|---|---|
| 1,180,614 A | 4/1916 | Simpson | |
| 3,304,362 A | 2/1967 | August | |
| 3,624,460 A | 11/1971 | Correll | |
| 3,640,705 A | 2/1972 | Selman et al. | |
| 3,829,969 A | 8/1974 | Fischbein et al. | |
| 3,844,921 A | 10/1974 | Benedict | |
| 4,010,759 A | 3/1977 | Boer | |
| 4,015,175 A | 3/1977 | Kendall et al. | |
| 4,107,762 A | 8/1978 | Shirn et al. | |
| 4,220,813 A * | 9/1980 | Kyle | 174/152 GM |
| 4,254,775 A | 3/1981 | Langer | |
| 4,385,029 A | 5/1983 | Desai | |
| 4,424,551 A | 1/1984 | Stevenson et al. | |
| 4,468,370 A | 8/1984 | Masumoto et al. | |
| 4,514,589 A | 4/1985 | Aldinger et al. | |
| 4,517,156 A | 5/1985 | Masumoto et al. | |
| 4,579,787 A | 4/1986 | Heidsiek et al. | |
| 4,678,868 A | 7/1987 | Kraska et al. | |
| 4,683,516 A | 7/1987 | Miller | |
| 4,791,391 A | 12/1988 | Linnell | |
| 4,940,858 A | 7/1990 | Taylor et al. | |

(Continued)

FOREIGN PATENT DOCUMENTS

EP    0331959 A2    9/1989

(Continued)

*Primary Examiner* — Niketa Patel
*Assistant Examiner* — Joseph Stoklosa

(57) ABSTRACT

Methods and apparatuses are provided for an electrical device that employs a feedthrough including a hermetic seal that seals an interior region of the electrical device. The electrical device includes an electrical contact disposed within the interior region of the electrical device, and a wire terminal that includes an encircled portion that is encircled by the feedthrough, and a first end that electrically connects with said electrical contact. When the electrical device is constructed, the first end of the wire terminal is coated with a conductive metal that is more resistant to oxidation than the wire terminal. The first end of the wire terminal is secured to the electrical contact using a mechanical device such as a crimping connector or a spring connector.

69 Claims, 6 Drawing Sheets

U.S. PATENT DOCUMENTS

| | | |
|---|---|---|
| 5,072,873 A | 12/1991 | Liu et al. |
| 5,104,755 A | 4/1992 | Taylor et al. |
| 5,131,388 A | 7/1992 | Pless et al. |
| 5,139,891 A | 8/1992 | Cowie et al. |
| 5,174,954 A | 12/1992 | Schaffer et al. |
| 5,245,999 A | 9/1993 | Dahlberg et al. |
| 5,290,371 A | 3/1994 | Cameron et al. |
| 5,298,218 A | 3/1994 | Groll et al. |
| 5,333,095 A | 7/1994 | Stevenson et al. |
| 5,338,509 A | 8/1994 | Coupland et al. |
| 5,366,496 A | 11/1994 | Dahl et al. |
| 5,370,663 A | 12/1994 | Lin |
| 5,406,444 A | 4/1995 | Seifried et al. |
| 5,431,875 A | 7/1995 | Cameron et al. |
| 5,531,003 A * | 7/1996 | Seifried et al. ............ 29/25.42 |
| 5,538,685 A | 7/1996 | Toyofuku et al. |
| 5,601,607 A * | 2/1997 | Adams .......................... 607/5 |
| 5,637,274 A | 6/1997 | Kitamura |
| 5,662,696 A | 9/1997 | Kroll et al. |
| 5,817,984 A | 10/1998 | Taylor et al. |
| 5,821,011 A | 10/1998 | Taylor et al. |
| 5,836,992 A | 11/1998 | Thompson et al. |
| 5,866,851 A | 2/1999 | Taylor et al. |
| 5,867,361 A | 2/1999 | Wolf et al. |
| 5,905,627 A | 5/1999 | Brendel et al. |
| 6,008,980 A * | 12/1999 | Stevenson et al. ............ 361/302 |
| 6,031,710 A | 2/2000 | Wolf et al. |
| 6,052,623 A | 4/2000 | Fenner et al. |
| 6,090,503 A | 7/2000 | Taylor et al. |
| 6,159,560 A * | 12/2000 | Stevenson et al. ............ 427/594 |
| 6,169,925 B1 | 1/2001 | Villaseca et al. |
| 6,248,190 B1 | 6/2001 | Stinson |
| 6,290,501 B1 | 9/2001 | Grau et al. |
| 6,349,025 B1 | 2/2002 | Fraley et al. |
| 6,414,835 B1 | 7/2002 | Wolf et al. |
| 6,490,148 B1 | 12/2002 | Allen et al. |
| 6,529,103 B1 | 3/2003 | Brendel et al. |
| 6,660,116 B2 | 12/2003 | Wolf et al. |
| 6,662,035 B2 | 12/2003 | Sochor |
| 6,765,779 B2 | 7/2004 | Stevenson et al. |
| 6,765,780 B2 | 7/2004 | Brendel et al. |
| 6,852,925 B2 | 2/2005 | Wolf et al. |
| 6,888,715 B2 | 5/2005 | Stevenson et al. |
| 6,899,976 B2 | 5/2005 | Larson et al. |
| 6,999,818 B2 | 2/2006 | Stevenson et al. |
| 7,012,192 B2 | 3/2006 | Stevenson et al. |
| 7,038,900 B2 | 5/2006 | Stevenson et al. |
| 7,145,076 B2 | 12/2006 | Knappen et al. |
| 7,174,219 B2 | 2/2007 | Wahlstrand et al. |
| 7,210,966 B2 | 5/2007 | Taylor et |
| 7,340,305 B2 | 3/2008 | Fischbach et al. |
| 7,354,488 B2 | 4/2008 | Klein et al. |
| 7,564,674 B2 | 7/2009 | Frysz et al. |
| 2003/0050549 A1 | 3/2003 | Sochor |
| 2003/0096162 A1 | 5/2003 | Lasater et al. |
| 2003/0179536 A1 | 9/2003 | Stevenson et al. |
| 2003/0213605 A1 | 11/2003 | Brendel et al. |
| 2004/0257747 A1 | 12/2004 | Stevenson et al. |
| 2005/0060003 A1 | 3/2005 | Taylor et al. |
| 2005/0201039 A1 | 9/2005 | Stevenson et al. |
| 2005/0222647 A1 | 10/2005 | Wahlstrand et al. |
| 2005/0247379 A1 | 11/2005 | Klein et al. |
| 2006/0247714 A1 | 11/2006 | Taylor et al. |
| 2006/0259093 A1 | 11/2006 | Stevenson et al. |
| 2006/0282126 A1 | 12/2006 | Fischbach et al. |
| 2007/0134985 A1 | 6/2007 | Frysz et al. |
| 2007/0260282 A1 | 11/2007 | Taylor et al. |
| 2008/0114413 A1 | 5/2008 | Fischbach et al. |
| 2010/0010560 A1 | 1/2010 | Taylor et al. |

FOREIGN PATENT DOCUMENTS

| | | |
|---|---|---|
| EP | 0331959 A3 | 1/1991 |
| EP | 0331959 B1 | 12/1994 |
| SU | 892492 | 12/1981 |
| WO | WO 91/06129 | 5/1991 |

\* cited by examiner

FEEDTHROUGH APPARATUS WITH NOBLE METAL-COATED LEADS

This is a continuation of application Ser. No. 10/661,919, filed Sep. 12, 2003, (pending), which is incorporated herein by reference.

FIELD OF THE INVENTION

The present invention relates to electrical devices that incorporate electrical feedthroughs, and to their method of fabrication. More particularly, the present invention relates to improving the conductivity of metal leads that are part of electrical feedthroughs, and also improving their connectivity with conductive contacts.

BACKGROUND OF THE INVENTION

Electrical feedthroughs serve the purpose of providing a conductive path extending between the interior of a hermetically sealed container and a point outside the container. The conductive path through the feedthrough comprises a conductor pin or terminal that is electrically insulated from the container. Many such feedthroughs are known in the art that provide the conductive path and seal the electrical container from its ambient environment. Such feedthroughs typically include a ferrule, and an insulative material such as a hermetic glass or ceramic seal that positions and insulates the pin within the ferrule. Electrical devices such as biorhythm sensors, pressure sensors, and implantable medical devices (IMD's) such as pulse generators and batteries often incorporate such feedthroughs. Sometimes it is necessary for an electrical device to include a capacitor within the ferrule and around the terminal, thus shunting any electromagnetic interference (EMI) at high frequencies at the entrance to the electrical device to which the feedthrough device is attached. Typically, the capacitor electrically contacts the pin lead and the ferrule.

Some of the more popular materials that are used as a feedthrough terminal are susceptible to oxide growth, which can act as an insulator instead of a conductor over the surface of the pin lead, particularly if the oxide growth is extensive. For instance, during fabrication of a feedthrough/capacitor combination the central terminal is subjected to one or more heat treatments. Even though feedthroughs are typically manufactured in an inert atmosphere, high temperatures will encourage oxidation if there is residual oxygen from a sealing gas or from dissociation of surface adsorbed water on fixtures and components. Oxidation of the terminal affects the conductivity of the pin lead and its ability to make good electrical connections with other elements. The ability for the surface oxidized pin terminal to be electrically connected to a contact would be particularly impaired if mechanical means such as crimping were employed to establish an electrical connection. This impairment is troublesome in cases where mechanical means might be less time consuming or less costly than other joining methods such as welding.

Accordingly, it is desirable to provide a method of manufacturing an electrical apparatus incorporating a feedthrough device wherein mechanical means are employed to establish an electrical connection between the feedthrough leads and a contact of the electrical apparatus. In addition, it is desirable to provide a feedthrough device that can be utilized in such a method. Furthermore, other desirable features and characteristics of the present invention will become apparent from the subsequent detailed description and the appended claims, taken in conjunction with the accompanying drawings and the foregoing technical field and background.

SUMMARY OF THE INVENTION

A medical device is provided that is efficiently manufactured. The medical device comprises an encasement, an electrical device disposed within the encasement, an electrical contact coupled to the electrical device, and a feedthrough assembly. The feedthrough assembly comprises a ferrule extending through the encasement and having an inner surface, a terminal extending through the ferrule and having a first end extending into the encasement, a conductive metal coating that is more resistant to oxidation than the terminal covering the first end of the terminal, and a body of insulation material disposed between the terminal and the inner wall for preventing the ferrule from electrically contacting the terminal. The medical device also comprises a connector for electrically coupling the first end to the electrical contact.

A feedthrough assembly is also provided that includes the feedthrough described above, and a connector that is connected to a first end of the feedthrough assembly terminal for electrically coupling the first end of the terminal to an electrical contact.

Also, a method of manufacturing a medical device is provided. The method comprises the steps of deploying an electrical device within an encasement, the electrical device being coupled to an electrical contact, and forming the above-described feedthrough assembly in the encasement. Then, the first end of the feedthrough assembly terminal is electrically coupled to the electrical contact using a connector.

BRIEF DESCRIPTION OF THE DRAWINGS

The present invention will hereinafter be described in conjunction with the following drawing figures, wherein like numerals denote like elements.

DETAILED DESCRIPTION OF THE DRAWINGS

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Figure 1:
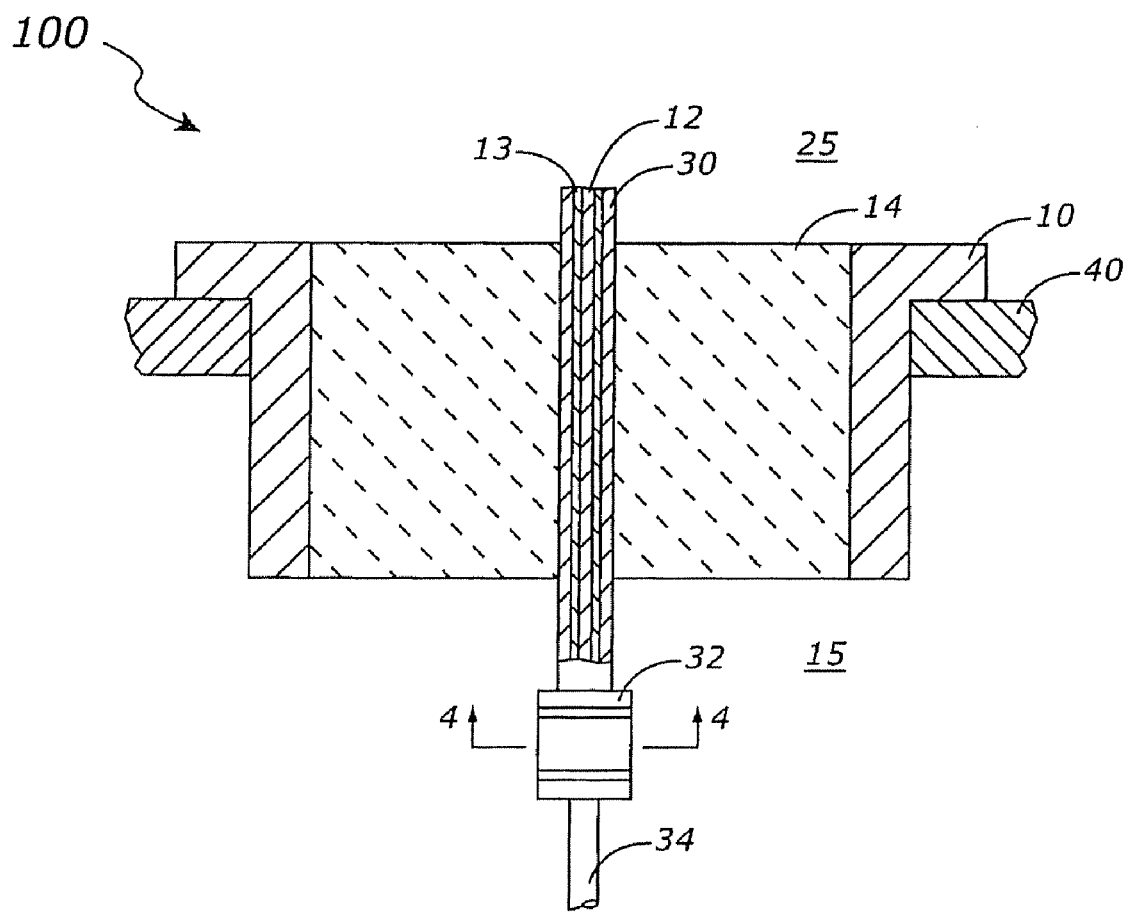
FIG. 1 is a sectional view of an electrical feedthrough that hermetically seals and electrically connects with a contact by way of a conductive metal-coated terminal, where the electrical connection is made using a mechanical joining device, according to an embodiment of the present invention.

Referring now to FIG. 1, there is depicted one embodiment of an electrical feedthrough 100 which is intended for use in conjunction with an electrical device, an exterior container 40 of the electrical device being in contact with the feedthrough 100. The term "electrical device" used hereafter refers to any device incorporating an electrical feedthrough, including but not limited to biorhythm sensors, pressure sensors, and various IMD's such as pulse generators and batteries. Although the discussion of the feedthrough device throughout the specification is directed to devices employing glass-to-metal, ceramic-to-metal, or ceramic-to-metal polymer type seals, it is to be understood that the principles of the invention are of general application to any feedthrough utilizing a pin lead for the purpose of making electrical connection to any contained electrical device which is to be sealed from its ambient environment. The principles of the invention are also applicable to multiple pin feedthroughs.

The feedthrough 100 of the present invention includes a center pin terminal 12, with a portion of the length of the terminal 12 passing through a ferrule 10. Electrical feedthroughs that are used in IMD's and other biological devices may inadvertently come into contact with body fluids. Thus, it is desirable that the terminal 12 be made of a bio-stable material. For example, the terminal 12 may consist of or include niobium, titanium, tantalum, and alloys of the metals, and other bio-stable conductive metals. Preferably, the terminal 12 is manufactured using a refractory metal. In a typical installation, one end of the terminal 12 extends through a capsule or container 40 into the interior 15 of the electrical device, and electrically connects with at least one internal contact 34. Another end of the terminal 12 extends to the exterior 25 of the electrical device.

The insulating material 14 surrounds a portion of the length of the terminal 12. In an exemplary embodiment of the invention, the insulating material 14 includes glass or glass-ceramic joined directly to conductor materials by heating or a ceramic joined to conductor materials by braze material by heating, or high dielectric polymers such as polyimides. If the insulating material is a ceramic material, the material is preferably ruby, sapphire or polycrystalline alumina. The composition of the insulating material 14 should be carefully selected to have thermal expansion characteristics that are compatible with the terminal 12. The insulating material 14 prevents a short circuit between the terminal 12 and the ferrule 10 or the container 40.

In order to ensure a tight seal between the glass 14 and the walls of the container 40, the ferrule 10 is disposed as a thin sleeve therebetween. Typically the ferrule 10 has an annular configuration, but may have any configuration suitable for use with the container for the electrical device. The ferrule 10 may be formed of titanium, niobium, tantalum, zirconium, any combination thereof, or any other suitable metal or combination of metals. The ferrule 10 is affixed to the inner surface of the container 40, preferably by welding although any other suitable means, such as gluing or soldering, may be used.

In order to prevent oxide formation on the terminal 12 and the contact resistance instability attributed to such oxide formation, the terminal 12 is coated with a thin film 30 of a conductive metal that is less easily oxidized than the terminal 12. Preferably, the conductive metal film 30 comprises a noble metal or an alloy of noble metals. The noble metals include gold, platinum, palladium, rhodium, ruthenium, and iridium. These metals and alloys thereof are highly resistant to oxidation, and consequently protect the terminal 12 from hot, humid, or even liquid environments. The protection provided by the noble metals and alloys thereof decrease the contact resistance, and therefore increase the stability of crimp connections between a contact and the terminal 12. The conductive metal film 30, hereinafter referred to as the noble metal film 30, is applied by DC magnetron sputtering or RF sputtering in an exemplary embodiment of the invention, although other conventional techniques may be used such as chemical vapor deposition, cladding, vacuum depositing, painting, other types of sputtering, etc. The noble metal film 30 is deposited at a minimum thickness of about 100 Å, and preferably is at a thickness ranging from about 3000 Å to about 7000 Å.

In an exemplary embodiment of the invention, an intermediate film 13 may be deposited on the terminal 12 prior to deposition of the noble metal film 30. The thin intermediate film 13 is a refractory metal, preferably titanium or niobium, and enhances the adhesion of subsequent metal depositions to the terminal 12. The intermediate film 13 is applied by any conventional technique such as sputtering, chemical vapor deposition, vacuum depositing, painting, or cladding, and is preferably applied using either DC magnetron sputtering or RF sputtering.

According to the embodiment of the invention depicted in FIG. 1, the noble metal film 30 coats the regions of the terminal 12 that are both within and outside the feedthrough device 100 in a continuous manner. The manufacturing process for this embodiment includes the step of coating the terminal 12 with the noble metal film 30 using an appropriate technique prior to forming the hermetic seal between the insulating material 14 and the terminal 12. When the insulating material 14 is a body of glass, the feedthrough seal is formed by applying molten glass between the terminal 12 and the ferrule 10, and allowing the molten glass to solidify. This process is generally referred to as "glassing" in the art. A ceramic material can also be included as insulation material, either in place of or together with a glass material.

The noble metal should be carefully selected to ensure that the noble metal film 30 does not disrupt the stability of the hermetic seal that would be formed between the insulating material 14 and the terminal 12 in the absence of the noble metal film 30. If the entire terminal 12 is coated with the noble metal 30 prior to forming the seal, then the noble metal 30 must be of the type which can readily react with or diffuse into the metal that forms the terminal 12. As a result of proper reactivity and diffusion between the two metals, the insulation material 14 will be able to wet and react with the material forming the terminal 12, and not only with the noble metal film 30. Following formation of the seal between the insulating material 14 and the terminal 12 extending therethrough, the ferrule 10 is affixed to the inner surface of the container for the electrical device using any conventional method, and preferably using a welding technique.

Figure 4:
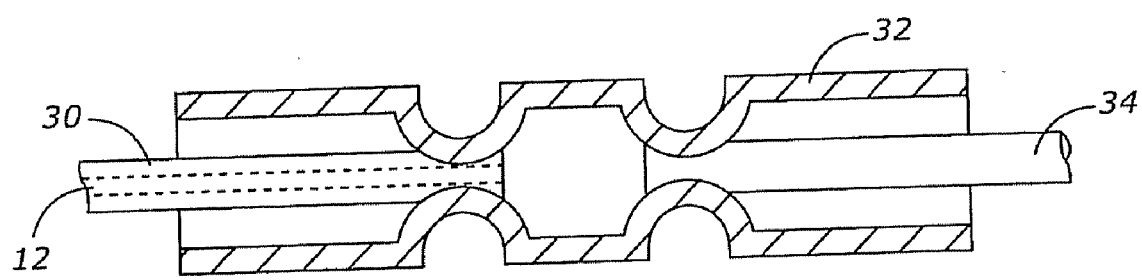
FIG. 4 is a cross sectional view of a crimping apparatus electrically coupling a noble metal-coated terminal to an electrical contact according to an embodiment of the invention.

An electrical connection between the terminal 12 and the contact 34 is secured by a crimping device according to one embodiment of the invention. Turning now to FIG. 4, a cross sectional view of a crimping device 32 is depicted, the crimping device 32 placing a mechanical force on both the terminal 12 coated with the noble metal film 30, and the contact 34. Many known crimping devices can be used in place of the simple crimping mechanism 32 depicted in FIG. 4. Because the terminal 12 is protected from oxidation due to the presence of the noble metal film 30, low resistance crimp connections between the terminal 12 and conventional contacts such as copper wires or cables may be provided in place of more complicated types of connections. Crimping connections are much less expensive than connections involving alloying or heat joining such as welding. Also, crimping is among the easiest and the least expensive of mechanical methods for joining terminals with other wires or cables. Consequently, the method of the present invention for crimping a noble metal film-coated terminal is a highly advantageous and cost saving option for designing electrical devices that employ feedthroughs to hermetically seal the interior components of the electrical devices.

Figure 5:
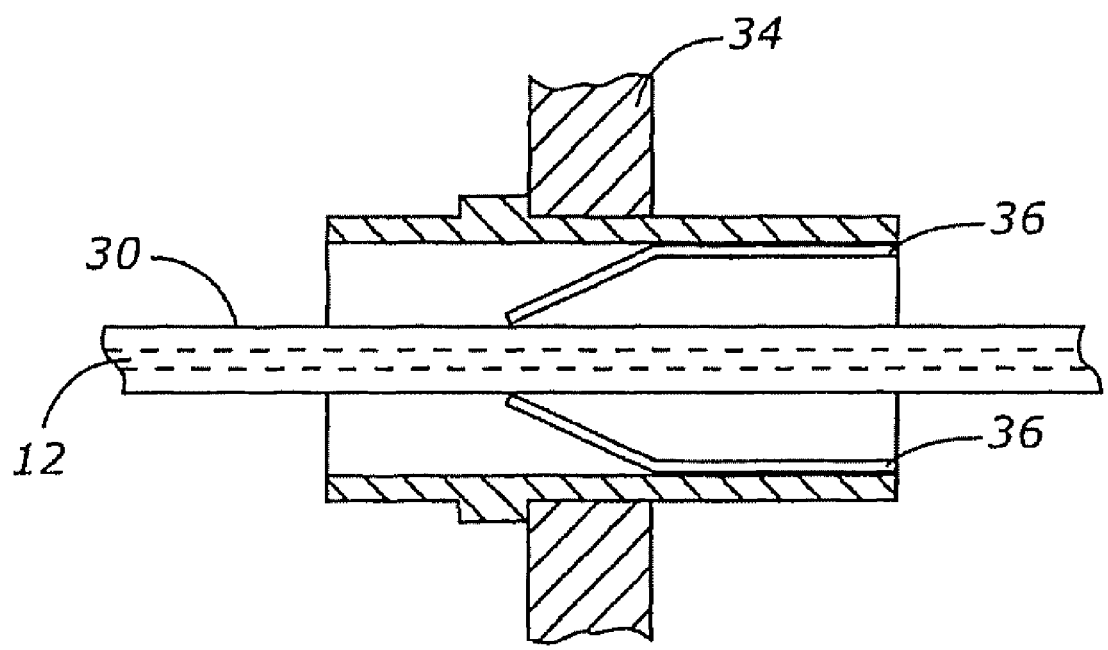
FIG. 5 is a cross sectional view of a spring connection electrically coupling a noble metal-coated terminal to an electrical contact according to one embodiment of the invention.

According to another embodiment, the electrical connection between the terminal 12 and the contact 34 is secured by a spring connection. FIG. 5 depicts a cross sectional view of a spring device 36, the spring device 36 placing a mechanical force on the terminal 12 coated with the noble metal film 30, and electrically coupling the terminal 12 with the contact 34. The spring device 36 shown in FIG. 5 is just one of many known spring devices that can be used according to the present invention.

Figure 2:
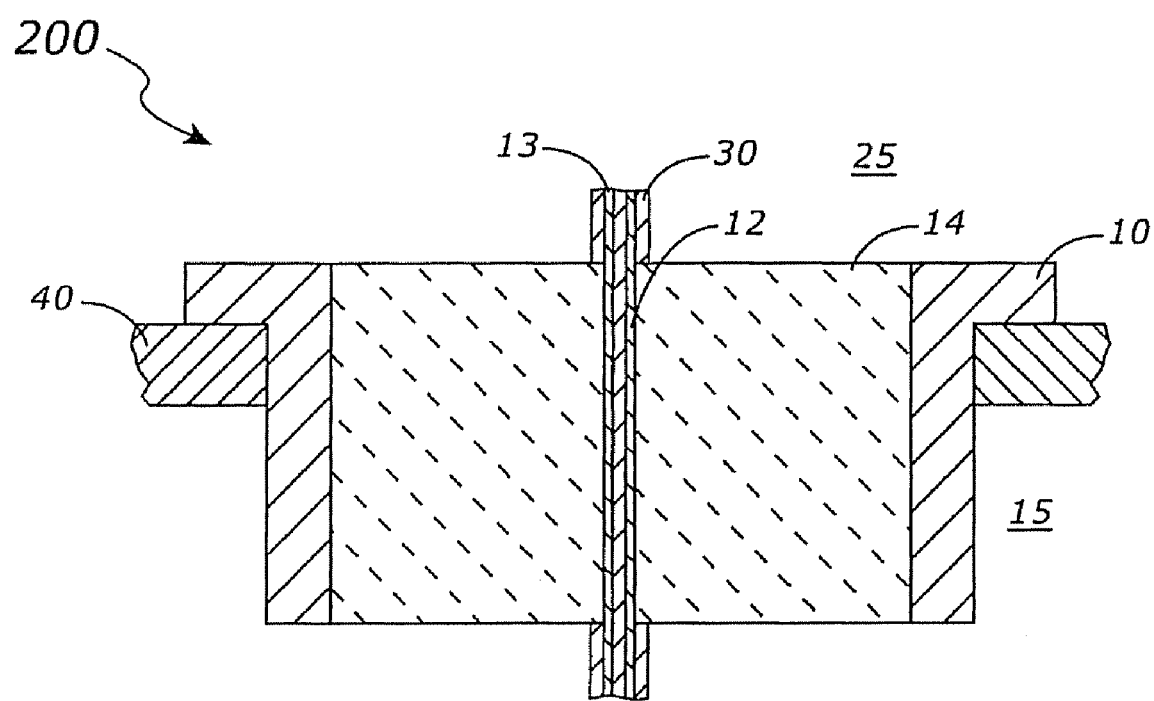
FIG. 2 is a sectional view of an electrical feedthrough that hermetically seals and electrically connects with a contact by way of a partially conductive metal-coated terminal, where the electrical connection is made using a mechanical joining device, according to an embodiment of the present invention.

Another embodiment of the invention is depicted in FIG. 2. Many of the features depicted in FIG. 2 are identical to those discussed above. Also, the connection between the terminal 12 and the contact 34 using a crimping device 34, a spring contact 34, or other surface contact is applicable to all embodiments of the present invention, even if not depicted in all of the drawings.

In the embodiment depicted in FIG. 2, the terminal 12 is not coated with a noble metal film 30 throughout the interior portion of the feedthrough device 200. The electrical device is manufactured by first inserting the terminal 12 into the feedthrough device 200, with the noble metal film 30 being either absent altogether, or absent from at least the regions of the terminal 12 that will be reacted with the insulating material 14 to form a hermetic seal. A sealing technique as described above is then performed to seal the insulation material 14 to the other feedthrough assembly components. Because of the absence of the noble metal film 30 in the seal region of the feedthrough 200, consideration need not be given for potential disruption of the stability of the hermetic seal that is to be formed between the insulating material 14 and the terminal 12. The exposed terminal 12 exterior to the feedthrough 200 is coated with the noble metal 30 after seal manufacture and consequently the noble metal 30 need not be of the type which can readily react with or diffuse into the metal that forms the terminal 12, although such properties may still be advantageous for other reasons. Following formation of the seal between the insulating material 14 and the terminal 12 extending therethrough, the ferrule 10 is affixed to the inner surface of the container for the electrical device using any conventional method, and preferably using a welding technique.

As mentioned above and depicted in FIG. 2, the noble metal film 30 is selectively deposited onto the terminal 12 in order to avoid having the noble metal in contact with the insulating material 14 during glassing or any other suitable sealing method. One way that the noble metal film 30 can be selectively deposited is by employing a method wherein the terminal 12 is masked with a masking material before the noble metal film 30 is formed thereon. The mask can be applied to the terminal 12 using chemical or mechanical masking techniques. The noble metal film 30 is then formed outside of the areas that will be critical sealing regions, and at least over the region of the terminal 12 that is to be crimped to the contact 34. The masking material is then removed. The selectively coated terminal is then inserted into the feedthrough 200 and the seal manufacturing method is performed.

Another way that the noble metal film 30 can be selectively deposited is by performing the seal manufacturing method with a terminal 12 that is completely free of any noble metal film. Then, the insulative path between the terminal 12 and the ferrule 10 or other metal serving as a conductor is isolated using chemical or mechanical masking methods. After isolating the conductors from one another, the noble metal film 30 is applied at least over the region of the terminal 12 that is to be crimped to the contact 34.

Figure 3:
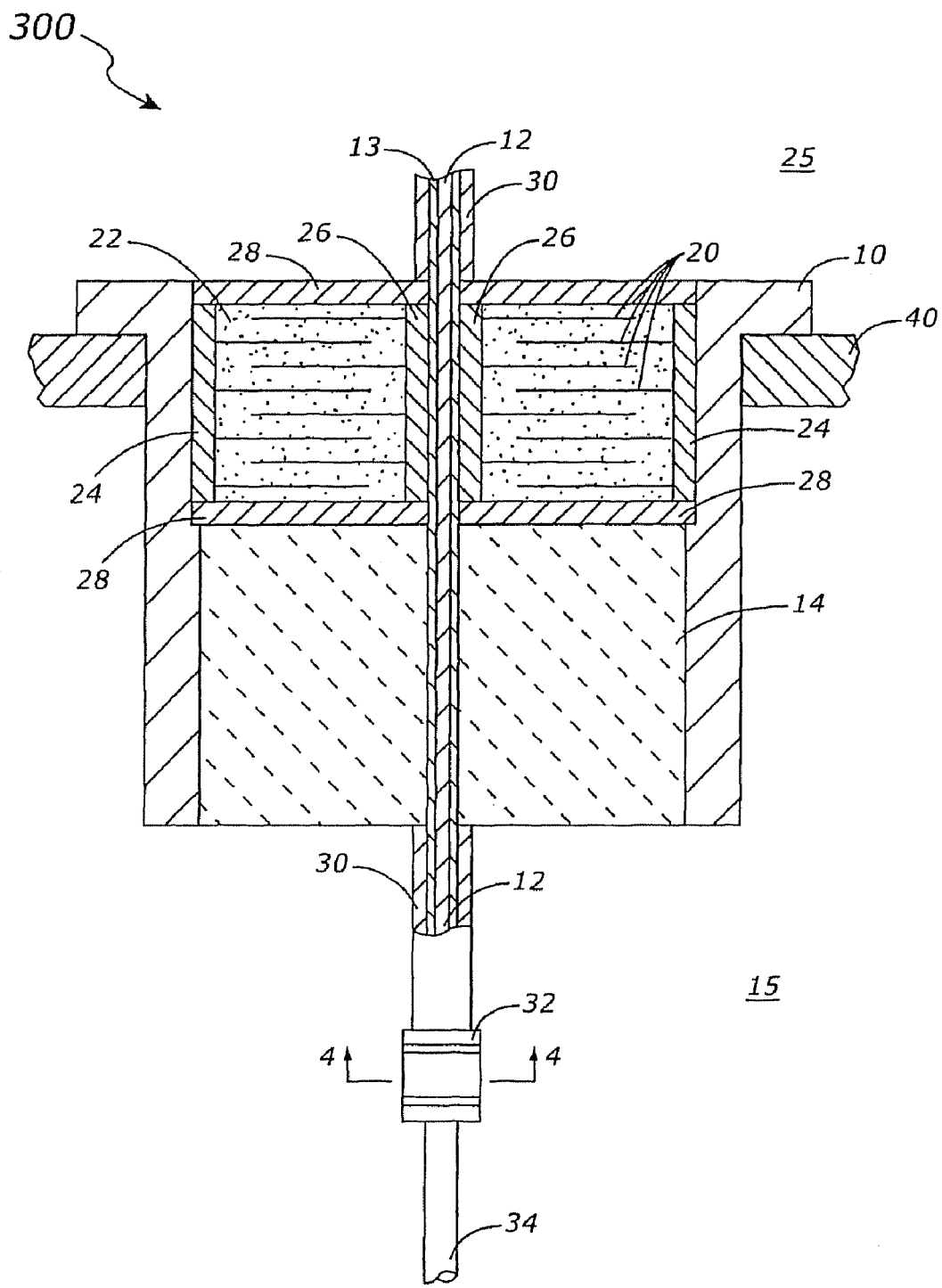
FIG. 3 is a sectional view of an electrical feedthrough that incorporates a capacitor and hermetically seals and electrically connects with a contact by way of a conductive metal-coated terminal, where the electrical connection is made using a mechanical joining device according to an embodiment of the present invention.

The embodiment of the invention depicted in FIG. 3 is similar to that of FIG. 2 in that the terminal 12 is not coated with a noble metal coating 30 throughout the interior portion of the feedthrough device 300. The method discussed above can be applied to an electrolytic capacitor feedthrough for providing a noble metal film 30 as a partial coating on the terminal 12 of the feedthrough 300. The feedthrough 300 includes a capacitor within the feedthrough ferrule 10. The capacitive structure may include a multi-layer ceramic structure of annular discoidal shape having several sets of thin, spaced apart, electrically conductive electrode plates 20 that are separated by thin layers of ceramic dielectric insulating material 22. The capacitor also includes first and second mutually isolated electrically conductive exterior and interior termination surfaces 24 and 26 and insulative end surfaces 28. The alternative methods for selectively coating the noble metal film 30 over the terminal 12 are employed in the same manner that they are employed in the embodiment depicted in FIG. 2.

Tests performed on the electrical device incorporating the feedthrough apparatus depicted in FIG. 1 revealed that the noble metal coating does not detrimentally affect the hermeticity of the seal provided by the feedthrough apparatus. Several examples of the configuration of the present invention were tested by first sputter coating approximately 7000 Å of gold, platinum, palladium, ruthenium and rhodium onto respective tantalum wire leads prior to hermetic seal manufacture. The leads were then subjected to a hermetic sealing process that included glassing insulative material onto the noble metal-coated terminals. The terminals were then crimped to standard gold plated copper-beryllium contacts and subjected to standard environmental testing. The testing involved exposing the crimped terminals and contacts to temperatures of 85° F. and 85% relative humidity for long periods of time. All wires were 0.011" In diameter.

Contact resistance was measure before and after testing. Table 1 below is a summary of the test results.

TABLE 1

| Resistance (mhoms) | Ta Wire | Pt Wire | Au Coated Ta Wire | Pt Coated Ta Wire | Pd Coated Ta Wire | Ru Coated Ta Wire | Rh Coated Ta Wire |
| --- | --- | --- | --- | --- | --- | --- | --- |
| Intl. Ave. | 146 | 7.52 | 23.8 | 10.73 | 9.4 | 10.16 | 10.87 |
| Std. Dev. | 93.2 | 0.19 | 9.03 | 0.64 | 0.69 | 0.86 | 0.85 |
| Shift Ave. (post test) | 104.3 | 40.6 | 59.1 | 49.17 | 0.78 | −0.21 | 2.17 |
| Std. Dev. | 144.6 | 0.37 | 54.2 | 101.5 | 1.5 | 3.21 | 1.85 |

The test results that are summarized in Table 1 show that significant improvements in both initial contact resistance and resistance shift resulted from coating tantalum wires with various noble metals, when compared with a contact involving bare tantalum wire. The improvements were especially significant when the noble metal film was a palladium, ruthenium, or rhodium coating. Similar improvements result from any of the noble metals as coatings of other refractory metal terminals.

Figure 6:
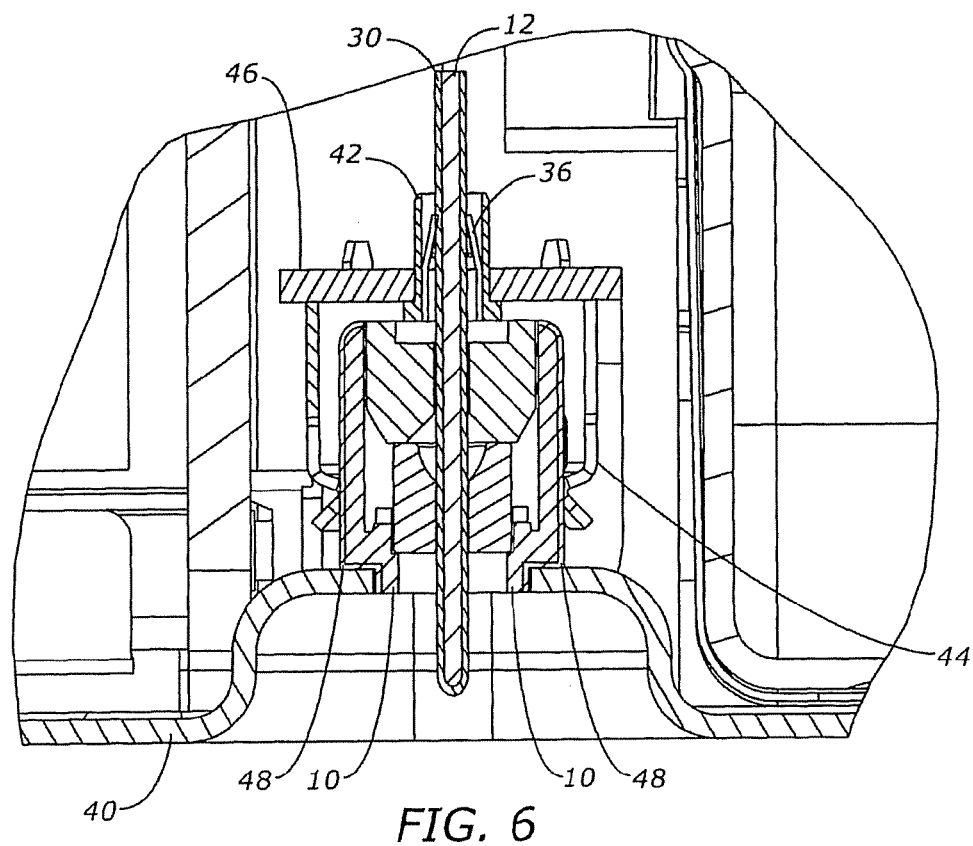
FIG. 6 is a cross sectional view of an electrical feedthrough that hermetically seals and electrically connects with a first contact by way of a conductive metal-coated terminal, and with a second contact by way of a conductive metal-coated ferrule, where both electrical connections are made using mechanical joining devices according to an embodiment of the present invention.
Figure 7:
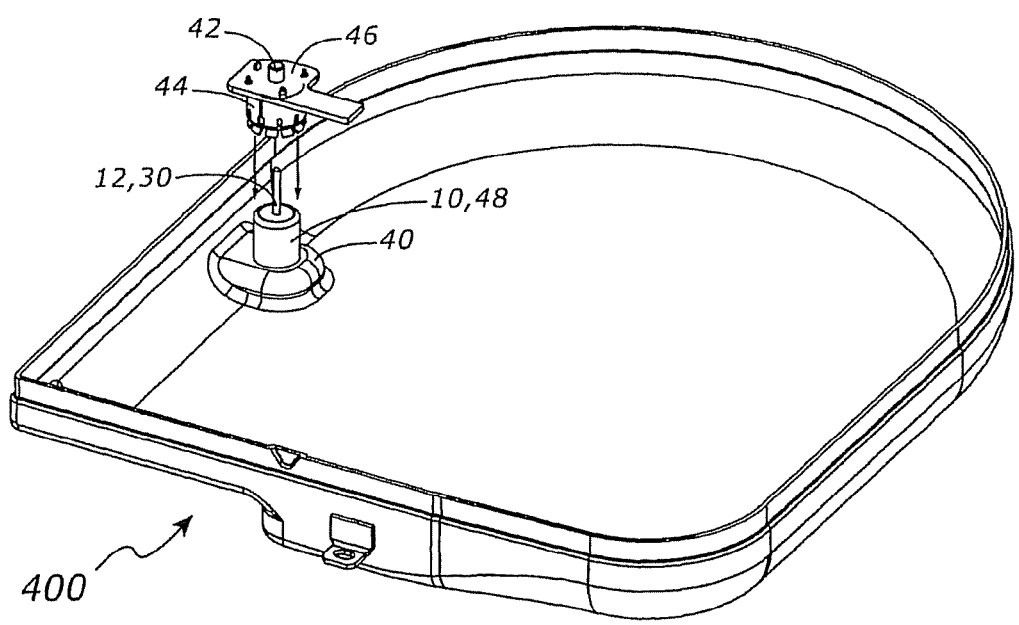
FIG. 7 is an isometric view of a medical device incorporating the electrical feedthrough illustrated in FIG. 6.

Turning now to FIGS. 6 and 7, another embodiment of the feedthrough assembly with metal coated leads according to the present invention is illustrated in the environment of a pacing device 400, although the use for the illustrated feedthrough assembly is in no way limited to such a device. Many of the features depicted in FIGS. 6 and 7 are identical to those discussed above. In FIGS. 6 and 7, the feedthrough terminal 12 coated with the noble metal film 30 and is securely engaged with a spring contact 36. The spring contact 36 is welded or otherwise joined to a conductive socket housing 42 which laterally surrounds the spring contact 36. The socket housing 42 is welded or otherwise secured to a flex circuit 46 which includes circuitry laminated within an insulative material. The spring contact 36 and the socket housing 42 couple the terminal 12 with selected circuitry within the flex circuit 46.

The ferrule 10 is also coated with a conductive metal film 48 according to this embodiment. The film 48 enables an electrical contact to be electrically coupled to, and mechanically engaged with, the ferrule 10 using a surface contact including but not limited to the crimping connection or the spring contact discussed above. The construction shown in FIGS. 6 and 7 includes a spring contact 44 that securely engages with the film 48 and electrically couples the ferrule 10 with selected circuitry within the flex circuit 46. The conductive metal film 48 can be formed from any metal that is less easily oxidized than the ferrule 10, but is preferably a noble metal or an alloy of noble metals.

Suitable noble metals include gold, platinum, palladium, rhodium, ruthenium, and iridium, although titanium, niobium and alloys of titanium or niobium are preferred. Just like the metals used for the film 30 that coats the feedthrough terminal 12, these metals and alloys thereof protect the ferrule from hot, humid, or liquid environments. The protection provided by the noble metals and alloys thereof decrease the contact resistance, and therefore increase the stability of surface connections between a contact and the ferrule 10. The film 48 is applied by DC magnetron sputtering or RF sputtering in an exemplary embodiment of the invention, although other conventional techniques may be used such as chemical vapor deposition, cladding, vacuum depositing, painting, other types of sputtering, etc. The film 48 is deposited at a minimum thickness of about 100 Å, and preferably is at a thickness ranging from about 3000 Å to about 7000 Å.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. An implantable medical device for delivering a therapy, the device comprising:

a hermetically-sealed container enclosing an electrical device;

a feedthrough coupled to the container, the feedthrough comprising:

a generally annular ferrule adapted to mate with an opening in the container;

insulating material disposed within and coupled to the ferrule; and a terminal conductor extending through and sealed to the insulating material and having a proximal portion disposed outside of the container and a distal portion disposed within the container, the terminal conductor comprising an inner core and an oxide-resistant cladding on the inner core, wherein an intermediate layer comprising a refractory metal is located between the inner core and the oxide resistant cladding; and a connection between the distal portion of the terminal conductor and the electrical device enclosed in the container.

2. A medical device according to claim 1, wherein the oxide resistant cladding comprises a noble metal or a noble metal alloy.

3. A medical device according to claim 1, wherein the oxide resistant cladding comprises a conductive metal selected from the group consisting of gold, platinum, palladium, rhodium, ruthenium, iridium and alloys thereof.

4. A medical device according to claim 1, wherein the oxide-resistant cladding comprises platinum.

5. A medical device according to claim 1, wherein the oxide-resistant cladding comprises platinum iridium alloy.

6. A medical device according to claim 1, wherein the connection between the distal portion of the terminal conductor and the electrical device enclosed in the container comprises a heat joined connection.

7. A medical device according to claim 6, wherein the heat joined connection comprises a weld.

8. A medical device according to claim 1, wherein the inner core comprises tantalum or niobium, and wherein the oxide-resistant cladding comprises a platinum or platinum-iridium alloy cladding.

9. A feedthrough for use in an implantable medical device of the type having a hermetically-sealed container containing an electrical device, the feedthrough comprising:

a generally annular ferrule adapted to mate with an opening in the container;

insulating material disposed within and coupled to the ferrule; and a terminal conductor extending through the insulating material and having a proximal portion disposed outside of the container and a distal portion disposed within the container, the terminal conductor comprising an inner core and an oxide-resistant cladding on the inner core, wherein an intermediate layer comprising a refractory metal is located between the inner core and the oxide resistant cladding.

10. The feedthrough of claim 9, wherein the inner core comprises tantalum, a tantalum alloy, niobium, or a niobium alloy.

11. The feedthrough of claim 10, wherein the oxide-resistant cladding comprises platinum or platinum-iridium.

12. The feedthrough of claim 9, further comprising a capacitive structure disposed within a portion of the ferrule, the capacitive structure being operatively coupled to the terminal conductor.

13. The feedthrough of claim 9, wherein the oxide resistant cladding is not located between the capacitive structure and the inner core of the terminal conductor.

14. The feedthrough of claim 9, wherein the oxide resistant cladding is not located between at least a portion of the insulating material and the inner core of the terminal conductor.

15. The feedthrough of claim 9, wherein the oxide resistant cladding comprises a conductive metal selected from the group consisting of gold, platinum, palladium, rhodium, ruthenium, iridium and alloys thereof.

16. An implantable medical device for delivering a therapy, the device comprising:
   a hermetically-sealed container enclosing an electrical device;
   a feedthrough coupled to the container, the feedthrough comprising:
      a generally annular ferrule adapted to mate with an opening in the container;
      insulating material disposed within and coupled to the ferrule; and
      a terminal conductor extending through and sealed to the insulating material and having a distal portion disposed within the container, the terminal conductor comprising an inner core and an oxide-resistant cladding on the inner core, wherein an intermediate layer comprising a refractory metal is located between the inner core and the oxide resistant cladding, and further wherein the oxide resistant coating is selected from the group consisting of a cladding, a paint, a vacuum deposited layer, a chemical vapor deposited layer, and a sputter deposited layer.

17. A medical device according to claim 16, wherein the oxide resistant coating comprises a noble metal or a noble metal alloy.

18. A medical device according to claim 16, wherein the oxide resistant coating comprises a conductive metal selected from the group consisting of gold, platinum, palladium, rhodium, ruthenium, iridium and alloys thereof.

19. A medical device according to claim 16, wherein the oxide-resistant coating comprises platinum.

20. A medical device according to claim 16, wherein the oxide-resistant coating comprises platinum iridium alloy.

21. A medical device according to claim 16, wherein the connection between the distal portion of the terminal conductor and the electrical device enclosed in the container comprises a heat joined connection.

22. A medical device according to claim 21, wherein the heat joined connection comprises a weld.

23. A medical device according to claim 16, wherein the inner core comprises tantalum or niobium, and wherein the oxide-resistant coating comprises a platinum or platinum-iridium alloy cladding.

24. An implantable medical device for delivering a therapy, the device comprising:
   a hermetically-sealed container enclosing an electrical device;
   a feedthrough coupled to the container, the feedthrough comprising:
      a generally annular ferrule adapted to mate with an opening in the container;
      insulating material disposed within and coupled to the ferrule; and
      a terminal conductor extending through and sealed to the insulating material and having a proximal portion disposed outside of the container and a distal portion disposed within the container, the terminal conductor comprising an inner core and an oxide-resistant cladding on the inner core, wherein an intermediate layer comprising a film comprising titanium is located between the inner core and the oxide resistant cladding; and
   a connection between the distal portion of the terminal conductor and the electrical device enclosed in the container.

25. A medical device according to claim 24, wherein the oxide resistant cladding comprises a noble metal or a noble metal alloy.

26. A medical device according to claim 24, wherein the oxide resistant cladding comprises a conductive metal selected from the group consisting of gold, platinum, palladium, rhodium, ruthenium, iridium and alloys thereof.

27. A medical device according to claim 24, wherein the oxide-resistant cladding comprises platinum.

28. A medical device according to claim 24, wherein the oxide-resistant cladding comprises platinum iridium alloy.

29. A medical device according to claim 24, wherein the connection between the distal portion of the terminal conductor and the electrical device enclosed in the container comprises a heat joined connection.

30. A medical device according to claim 29, wherein the heat joined connection comprises a weld.

31. A medical device according to claim 24, wherein the inner core comprises tantalum or niobium, and wherein the oxide-resistant cladding comprises a platinum or platinum-iridium alloy cladding.

32. An implantable medical device for delivering a therapy, the device comprising:
   a hermetically-sealed container enclosing an electrical device;
   a feedthrough coupled to the container, the feedthrough comprising:
      a generally annular ferrule adapted to mate with an opening in the container;
      insulating material disposed within and coupled to the ferrule; and
      a terminal conductor extending through and sealed to the insulating material and having a proximal portion disposed outside of the container and a distal portion disposed within the container, the terminal conductor comprising an inner core and an oxide-resistant cladding on the inner core, wherein an intermediate layer comprising a film comprising niobium is located between the inner core and the oxide resistant cladding; and
   a connection between the distal portion of the terminal conductor and the electrical device enclosed in the container.

33. A medical device according to claim 32, wherein the oxide resistant cladding comprises a noble metal or a noble metal alloy.

34. A medical device according to claim 32, wherein the oxide resistant cladding comprises a conductive metal selected from the group consisting of gold, platinum, palladium, rhodium, ruthenium, iridium and alloys thereof.

35. A medical device according to claim 32, wherein the oxide-resistant cladding comprises platinum.

36. A medical device according to claim 32, wherein the oxide-resistant cladding comprises platinum iridium alloy.

37. A medical device according to claim 32, wherein the connection between the distal portion of the terminal conductor and the electrical device enclosed in the container comprises a heat joined connection.

38. A medical device according to claim 37, wherein the heat joined connection comprises a weld.

39. A medical device according to claim 32, wherein the inner core comprises tantalum or niobium, and wherein the oxide-resistant cladding comprises a platinum or platinum-iridium alloy cladding.

40. A feedthrough for use in an implantable medical device of the type having a hermetically-sealed container containing an electrical device, the feedthrough comprising:
   a generally annular ferrule adapted to mate with an opening in the container;
   insulating material disposed within and coupled to the ferrule; and
   a terminal conductor extending through the insulating material and having a proximal portion disposed outside of the container and a distal portion disposed within the container, the terminal conductor comprising an inner core and an oxide-resistant cladding on the inner core, wherein an intermediate layer comprising titanium is located between the inner core and the oxide-resistant cladding.

41. The feedthrough of claim 40, wherein the inner core comprises tantalum, a tantalum alloy, niobium, or a niobium alloy.

42. The feedthrough of claim 41, wherein the oxide-resistant cladding comprises platinum or platinum-iridium.

43. The feedthrough of claim 40, further comprising a capacitive structure disposed within a portion of the ferrule, the capacitive structure being operatively coupled to the terminal conductor.

44. The feedthrough of claim 40, wherein the oxide resistant cladding is not located between the capacitive structure and the inner core of the terminal conductor.

45. The feedthrough of claim 40, wherein the oxide resistant cladding is not located between at least a portion of the insulating material and the inner core of the terminal conductor.

46. The feedthrough of claim 40, wherein the oxide resistant cladding comprises a conductive metal selected from the group consisting of gold, platinum, palladium, rhodium, ruthenium, iridium and alloys thereof.

47. A feedthrough for use in an implantable medical device of the type having a hermetically-sealed container containing an electrical device, the feedthrough comprising:
   a generally annular ferrule adapted to mate with an opening in the container;
   insulating material disposed within and coupled to the ferrule; and
   a terminal conductor extending through the insulating material and having a proximal portion disposed outside of the container and a distal portion disposed within the container, the terminal conductor comprising an inner core and an oxide-resistant cladding on the inner core, wherein an intermediate layer comprising niobium is located between the inner core and the oxide resistant cladding.

48. The feedthrough of claim 47, wherein the inner core comprises tantalum, a tantalum alloy, niobium, or a niobium alloy.

49. The feedthrough of claim 48, wherein the oxide-resistant cladding comprises platinum or platinum-iridium.

50. The feedthrough of claim 47, further comprising a capacitive structure disposed within a portion of the ferrule, the capacitive structure being operatively coupled to the terminal conductor.

51. The feedthrough of claim 47, wherein the oxide resistant cladding is not located between the capacitive structure and the inner core of the terminal conductor.

52. The feedthrough of claim 47, wherein the oxide resistant cladding is not located between at least a portion of the insulating material and the inner core of the terminal conductor.

53. The feedthrough of claim 47, wherein the oxide resistant cladding comprises a conductive metal selected from the group consisting of gold, platinum, palladium, rhodium, ruthenium, iridium and alloys thereof.

54. An implantable medical device for delivering a therapy, the device comprising:
   a hermetically-sealed container enclosing an electrical device;
   a feedthrough coupled to the container, the feedthrough comprising:
      a generally annular ferrule adapted to mate with an opening in the container;
      insulating material disposed within and coupled to the ferrule; and
      a terminal conductor extending through and sealed to the insulating material and having a distal portion disposed within the container, the terminal conductor comprising an inner core and an oxide-resistant coating on the inner core, wherein an intermediate layer comprising a film comprising titanium is located between the inner core and the oxide resistant coating, and further wherein the oxide resistant coating is selected from the group consisting of a cladding, a paint, a vacuum deposited layer, a chemical vapor deposited layer, and a sputter deposited layer.

55. A medical device according to claim 54, wherein the oxide resistant coating comprises a noble metal or a noble metal alloy.

56. A medical device according to claim 54, wherein the oxide resistant coating comprises a conductive metal selected from the group consisting of gold, platinum, palladium, rhodium, ruthenium, iridium and alloys thereof.

57. A medical device according to claim 54, wherein the oxide-resistant coating comprises platinum.

58. A medical device according to claim 54, wherein the oxide-resistant coating comprises platinum iridium alloy.

59. A medical device according to claim 54, wherein the connection between the distal portion of the terminal conductor and the electrical device enclosed in the container comprises a heat joined connection.

60. A medical device according to claim 59, wherein the heat joined connection comprises a weld.

61. A medical device according to claim 54, wherein the inner core comprises tantalum or niobium, and wherein the oxide-resistant coating comprises a platinum or platinum-iridium alloy cladding.

62. An implantable medical device for delivering a therapy, the device comprising:
   a hermetically-sealed container enclosing an electrical device;
   a feedthrough coupled to the container, the feedthrough comprising:
      a generally annular ferrule adapted to mate with an opening in the container;
      insulating material disposed within and coupled to the ferrule; and
      a terminal conductor extending through and sealed to the insulating material and having a distal portion disposed within the container, the terminal conductor comprising an inner core and an oxide-resistant coating on the inner core, wherein an intermediate layer comprising a film comprising niobium is located between the inner core and the oxide resistant coating, and further wherein the oxide resistant coating is selected from the group consisting of a cladding, a paint, a vacuum deposited layer, a chemical vapor deposited layer, and a sputter deposited layer.

63. A medical device according to claim 62, wherein the oxide resistant coating comprises a noble metal or a noble metal alloy.

64. A medical device according to claim 62, wherein the oxide resistant coating comprises a conductive metal selected from the group consisting of gold, platinum, palladium, rhodium, ruthenium, iridium and alloys thereof.

65. A medical device according to claim 62, wherein the oxide-resistant coating comprises platinum.

66. A medical device according to claim 62, wherein the oxide-resistant coating comprises platinum iridium alloy.

67. A medical device according to claim 62, wherein the connection between the distal portion of the terminal conductor and the electrical device enclosed in the container comprises a heat joined connection.

68. A medical device according to claim 67, wherein the heat joined connection comprises a weld.

69. A medical device according to claim 62, wherein the inner core comprises tantalum or niobium, and wherein the oxide-resistant coating comprises a platinum or platinum-iridium alloy cladding.

* * * * *